United States Patent
Matmour et al.

(10) Patent No.: US 11,180,596 B2
(45) Date of Patent: Nov. 23, 2021

(54) PROCESS FOR PREPARING A STATISTICAL COPOLYMER BASED ON ACYCLIC DIENE MONOMERS AND CYCLIC DIENE MONOMERS, COPOLYMERS AND COMPOSITIONS CONTAINING SAME

(71) Applicant: COMPAGNIE GENERALE DES ETABLISSEMENTS MICHELIN, Clermont-Ferrand (FR)

(72) Inventors: Rachid Matmour, Clermont-Ferrand (FR); Robert Ngo, Clermont-Ferrand (FR); Benoît Schnell, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 0 days.

(21) Appl. No.: 16/626,809

(22) PCT Filed: Jun. 28, 2018

(86) PCT No.: PCT/FR2018/051584
§ 371 (c)(1),
(2) Date: Dec. 26, 2019

(87) PCT Pub. No.: WO2019/002770
PCT Pub. Date: Jan. 3, 2019

(65) Prior Publication Data
US 2020/0131292 A1 Apr. 30, 2020

(30) Foreign Application Priority Data

Jun. 30, 2017 (FR) ...................................... 1756120

(51) Int. Cl.
| C08F 236/06 | (2006.01) |
| B60C 1/00 | (2006.01) |
| C08F 232/06 | (2006.01) |
| C08F 236/10 | (2006.01) |
| C07C 11/12 | (2006.01) |
| C07C 11/107 | (2006.01) |

(52) U.S. Cl.
CPC .............. *C08F 236/06* (2013.01); *B60C 1/00* (2013.01); *C07C 11/107* (2013.01); *C07C 11/12* (2013.01); *C08F 232/06* (2013.01); *C08F 236/10* (2013.01); *C08F 2800/10* (2013.01); *C08F 2800/20* (2013.01)

(58) Field of Classification Search
CPC ..... C08F 236/045; C08F 232/06; C07C 11/12
See application file for complete search history.

(56) References Cited

U.S. PATENT DOCUMENTS

| 3,935,177 A | 1/1976 | Muller et al. |
| 6,562,923 B1 | 5/2003 | Robert et al. |
| 2015/0274896 A1 | 10/2015 | Matmour et al. |

FOREIGN PATENT DOCUMENTS

| EP | 1829906 A1 | 3/2006 |
| JP | 2015212321 A * | 11/2015 |
| WO | 0220623 A1 | 3/2002 |
| WO | 2014053509 A1 | 4/2014 |

OTHER PUBLICATIONS

Wang, Weiyu, "Novel Thermoplastic Elastomers based on Benzofulvene: Synthesis and Mechanical Properties." PhD diss., University of Tennessee, 2015. (Year: 2015).*
Matsumoto, A. et al., "Radical Copolymerization of N-Phenylmaleimide and Diene Monomers in Competition with Diels-Alder Reaction". Journal of Polymer Science, Part A: Polymer Chemistry 2016, 54(22), 3616-3625. (Year: 2016).*
Liu, B et al., "Coordination Polymerization of Renewable 3-Methylenecyclopentene with Rare-Earth-Metal Precursors". Angewandte Chemie, International Edition 2017, 56(16), 4560-4564. (Year: 2017).*
Kobayashi, S. et al., "Controlled Polymerization of a Cyclic Diene Prepared from the Ring-Closing Metathesis of a Naturally Occurring Monoterpene". Journal of the American Chemical Society 2009, 131(23), 7960-7961. (Year: 2009).*
Imanishi, Y. et al., "Cationic Polymerization of 3-Methylenecyclohexene and 2-Methyl-1,3-pentadiene". Die Makromolekulare Chemie 1974, 175(6), 1761-1776. (Year: 1974).*
Kosaka, Y. et al., "Living Anionic Polymerization of Benzofulvene in Hydrocarbon Solvent". Macromol. Symp. 2015, 350, 55-66. (Year: 2015).*
International Search Report and Written Report for corresponding International Application No. PCT/FR2018/051584 dated Nov. 14, 2018.
Itaru Natori and Shohei Inoue: Living Anionic Polymerization of 1,3-cyclohexadiene with the n-Butyllithium/N,N,N,N-Tetramethylethylene diamine System. Copolymerization and Block Copolymerization with Styrene, Butadiene, and Isoprene, Macromolecules, vol. 4, No. 31, Jan. 31, 1998 (Jan. 31, 1198), pp. 982-987, XP992779116.

* cited by examiner

Primary Examiner — Richard A Huhn
(74) Attorney, Agent, or Firm — Dickinson Wright PLLC

(57) ABSTRACT

A process for preparing a random copolymer based on at least one acyclic diene monomers and on at least one cyclic diene monomer is provided. The process comprises a step of copolymerization, in the presence of a polar agent and an anionic initiator in a polymerization solvent, of at least one acyclic diene monomer and of at least one cyclic diene monomer of which one C=C double bond is endocyclic and conjugated to an exocyclic C=C double bond, at a polymerization temperature below 80° C. A molar ratio of the polar agent/function(s) of the anionic initiator capable of initiating anionic polymerization being greater than 0.1.
Copolymers based on at least one acyclic diene monomer and on at least one cyclic diene monomer and the compositions containing them are also provided.

19 Claims, No Drawings

PROCESS FOR PREPARING A STATISTICAL COPOLYMER BASED ON ACYCLIC DIENE MONOMERS AND CYCLIC DIENE MONOMERS, COPOLYMERS AND COMPOSITIONS CONTAINING SAME

This application is a 371 national phase entry of PCT/FR2018/051584 filed on 28 Jun. 2018, which claims benefit of French Patent Application No. 1756120, filed 30 Jun. 2017, the entire contents of which are incorporated herein by reference for all purposes.

BACKGROUND

1. Technical Field

The present invention relates to a process for synthesizing random copolymers comprising, within the main polymer chain, rings comprising at least one double bond, to such copolymers and to the compositions containing them.

2. Related Art

The chemical structure of a polymer generally has an impact on the chemical and physical properties of the polymer, and also the properties of the compositions containing it.

The Applicant has thus sought to copolymerize acyclic diene monomers, such as 1,3-butadiene, with cyclic monomers. Random copolymers are particularly sought. During their research, the Applicant has observed that with a monomer such as cyclohexadiene, copolymerization tests with 1,3-butadiene or isoprene did not lead to random copolymers, the formation of blocks being favoured, or the side reactions being too significant. These observations have confirmed the results reported by Natori (Macromolecules 1998, 31, 982-987) demonstrating that during the copolymerization of cyclohexadiene and isoprene or of cyclohexadiene and styrene, the incorporation of the isoprene or of the styrene is much faster than that of the cyclohexadiene and leads to diblock copolymers being obtained.

SUMMARY

In the pursuit of their research, the Applicant has discovered that it was possible to randomly insert cyclic units comprising at least one double bond using particular monomers and under particular operating conditions.

Thus, a first subject of the invention is a process for preparing a random copolymer based on acyclic diene monomers and on cyclic diene monomers, characterized in that it comprises a step of copolymerization, in the presence of a polar agent and an anionic initiator in a polymerization solvent, of at least one acyclic diene monomer and of at least one cyclic diene monomer of which one C=C double bond is endocyclic and conjugated to an exocyclic C=C double bond, at a polymerization temperature below 80° C., the [polar agent/function of the anionic initiator] molar ratio being greater than 0.1.

In particular, the [polar agent/function of the anionic initiator] molar ratio is greater than or equal to 0.3.

Advantageously, the acyclic diene monomer is a conjugated diene monomer, preferably 1,3-butadiene or isoprene.

Advantageously, the cyclic diene monomer is a monomer corresponding to the following formula (I):

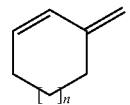

(I)

where n=0 or 1,
preferably 3-methylenecyclopentene.

In particular, in the process according to the present invention, a vinylaromatic compound having from 8 to 20 carbon atoms, advantageously styrene, is also copolymerized.

Advantageously, the polar agent is a tetraalkyldiamine, especially N,N,N',N'-tetramethylethylenediamine.

Advantageously, the anionic initiator contains an alkali metal, more advantageously the anionic initiator is an organolithium compound.

In particular, the polymerization temperature varies from 45° C. to 70° C., preferably from 50° C. to 60° C.

Another subject of the invention is a random copolymer comprising, randomly distributed within the main linear chain of the copolymer, unsaturated units derived from at least one acyclic diene monomer and cyclic units derived from at least one cyclic diene monomer of which one C=C double bond is endocyclic and conjugated to an exocyclic C=C double bond.

In particular, the acyclic diene monomer is a conjugated diene monomer, preferably 1,3-butadiene or isoprene.

In particular, the cyclic diene monomer is a monomer corresponding to the following formula (I):

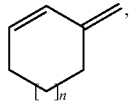

(I)

preferably 3-methylenecyclopentene.

Advantageously, the copolymer according to the invention also comprises units derived from a vinylaromatic compound having from 8 to 20 carbon atoms, advantageously styrene.

Advantageously, the molar percentage of units derived from the cyclic diene monomer, relative to the total number of units, is at least 5%, advantageously at least 10%.

In particular, the molar percentage of units derived from the cyclic diene monomer, relative to the total number of units, is less than 50%, advantageously less than 30%.

Another subject of the invention is a copolymer capable of being obtained by the process according to the invention.

In particular, the copolymer according to the invention is an elastomer.

Another subject of the invention is a composition comprising the copolymer according to the invention.

Another subject of the invention is a tyre, of which one of its constituent elements comprises a composition according to the invention.

In the present description, any interval of values denoted by the expression "from a to b" represents the range of values extending from a up to b (i.e. end points a and b included). Any interval "between a and b" represents the range of values extending from more than a to less than b (i.e. end points a and b excluded).

An "unsaturated unit" is understood to mean a unit derived from a diene monomer and comprising a double bond.

A "random distribution" is understood to mean a distribution of the constituent units of the copolymer that obeys a statistical law. A "polar agent" is understood to mean a molecule in which the distribution of the partial charges is not symmetrical, inducing a dipole moment in the molecule.

A "function of the anionic initiator" is understood to mean the function(s) capable of initiating the anionic polymerization. When the anionic initiator is a compound containing an alkali metal, each alkali metal is a function of the anionic initiator.

A "ring comprising at least one double bond" is understood to mean a ring comprising at least one endocyclic or exocyclic C=C double bond.

The cyclic diene monomer of which one C=C double bond is endocyclic and conjugated to an exocyclic C=C double bond may also be referred to, within the context of the present description, by the terms "cyclic diene monomer".

The compounds mentioned in the description and participating in the preparation of rubber compositions or polymers can be of fossil or biobased origin. In the latter case, they may be, partially or completely, derived from biomass or be obtained from renewable starting materials derived from biomass. The monomers are concerned in particular.

I-DETAILED DESCRIPTION OF EXAMPLE EMBODIMENTS

I.1. Process According to Examples of the Invention

I.1.1 Monomers

In the process according to the invention, use is made of at least one acyclic diene monomer and at least one cyclic diene monomer of which one C=C double bond is endocyclic and conjugated to an exocyclic C=C double bond.

According to the invention, these monomers are inserted randomly.

According to the invention, the diene monomer is inserted according to a sequence of 1,4-type or of 1,2-type, or in the form of a ring, advantageously randomly and independently.

As acyclic diene monomer, use may be made, according to the process in accordance with the invention, of any conjugated diene monomer having from 4 to 12 carbon atoms. 1,3-Butadiene, 2-methyl-1,3-butadiene (also denoted isoprene), 2,3-di($C_1$ to $C_5$ alkyl)-1,3-butadienes, such as, for example, 2,3-dimethyl-1,3-butadiene, 2,3-diethyl-1,3-butadiene, 2-methyl-3-ethyl-1,3-butadiene or 2-methyl-3-isopropyl-1,3-butadiene, phenyl-1,3-butadiene, 1,3-pentadiene, 2,4-hexadiene, etc. and mixtures thereof are suitable. The acyclic diene monomer is preferably 1,3-butadiene or isoprene.

As cyclic diene monomer, use may be made, according to the process in accordance with the invention, of any cyclic conjugated diene monomer of which one C=C double bond is endocyclic and conjugated to an exocyclic C=C double bond.

In particular, the monomer corresponds to the following formula (I):

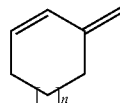

where n=0 or 1, advantageously n=0.

The cyclic diene monomer is preferably 3-methylenecyclopentene.

The cyclic conjugated diene is inserted in the form of a ring comprising an endocyclic double bond or in the form of a ring comprising an exocyclic double bond.

In addition to these monomers, at least one other monomer can also be copolymerized. This other monomer may be a vinylaromatic compound having from 8 to 20 carbon atoms. The following are suitable as vinylaromatic compound: styrene, ortho-, meta- or para-methylstyrene, the "vinyltoluene" commercial mixture, para-(tert-butyl)styrene, methoxystyrenes, vinylmesitylene, divinylbenzene and vinylnaphthalene. This other monomer is preferably styrene.

The monomers copolymerize by anionic polymerization.

The reaction mixture advantageously comprises, relative to the total weight of the monomers, at least 20% by weight of cyclic diene monomer. The reaction mixture may advantageously comprise up to 55% by weight of cyclic diene monomer, relative to the total weight of the monomers.

According to a variant of the invention, the reaction mixture comprises, relative to the total weight of the monomers, from 25% to 45% by weight of cyclic diene monomer. According to another variant of the invention, the reaction mixture comprises, relative to the total weight of the monomers, from 45% to 55% by weight of cyclic diene monomer.

The reaction mixture advantageously comprises, relative to the total weight of the monomers, at least 45% by weight of acyclic diene monomer. The reaction mixture may advantageously comprise up to 80% by weight of acyclic diene monomer, relative to the total weight of the monomers.

According to a variant of the invention, the reaction mixture comprises, relative to the total weight of the monomers, from 55% to 75% by weight of acyclic diene monomer.

According to another variant of the invention, the reaction mixture comprises, relative to the total weight of the monomers, from 45% to 55% by weight of acyclic diene monomer.

In addition to the monomers involved, the process according to the invention is also characterized by the presence of a polar agent.

I.1.2 Polar Agent and Anionic Initiator

The presence of a polar agent is required to obtain the desired copolymer.

Thus, in the process according to the invention, the [polar agent/function of the anionic initiator] molar ratio is greater than 0.1, advantageously greater than 0.3, more advantageously greater than 0.4. The [polar agent/function of the anionic initiator] molar ratio may range up to 3, advantageously up to 2.

Any type of polar agent may be used.

In particular, the polar agent may be a non-chelating polar agent or a chelating polar agent. The chelating polar agent is an organic compound which has on at least two atoms at least one non-binding doublet. In contrast, a non-chelating polar agent is an organic compound which has at most one non-binding doublet.

Notably, as non-chelating polar agents, mention may be made of Lewis bases of ether or tertiary amine type, or disulfides. In particular, use may be made of ethers such as diethyl ether, di-n-propyl ether, diisopropyl ether, diphenyl ether, anisole or else cyclic ethers such as tetrahydrofuran or dioxane. Use may also be made of tertiary amines as non-chelating polar agent, such as trialkylamines, in particular trimethylamine or triethylamine, cyclic amines, in particular N-methylmorpholine or N-ethylmorpholine. In particular, chelating polar agents can be used. In particular, use may be made of polyethers such as ethylene glycol dimethyl ether, ethylene glycol diethyl ether, diethylene glycol dimethyl ether or diglyme, diethylene glycol diethyl ether or triethylene glycol dimethyl ether or triglyme. Use may also be made of tetraalkyldiamines, in particular N, N, N',N'-tetramethylethylenediamine or TMEDA, 1,4-diazabicyclo[2.2.2]octane or DABCO, or use may be made of phosphorus derivatives such as hexamethylphosphoramide or HMPA. Preferably, the polar agent is a tetraalkyldiamine.

Use may be made, as polymerization initiator, of any known monofunctional or polyfunctional anionic initiator. However, an initiator containing an alkali metal such as lithium, sodium or potassium is preferentially used, and very particularly an initiator containing lithium.

Suitable organolithium initiators are in particular those comprising at least one carbon-lithium bond or at least one nitrogen-lithium bond. The number of carbon-lithium or nitrogen-lithium bonds may vary up to 12 bonds, more particularly up to 4 bonds. Suitable organolithium initiators comprising one or more carbon-lithium bonds are, for example, aliphatic organolithium compounds such as ethyllithium, n-butyllithium (n-BuLi), s-butyllithium (s-BuLi), isobutyl lithium, polymethylene dilithium compounds such as 1,4-dilithiobutane, 1,4-dilithiotetraphenylbutane, dilithiated initiators derived from the reaction of an organolithium compound with an aliphatic divinyl compound or an aromatic divinyl compound, in particular the reaction of s-butyllithium with dialkenylbenzenes, such as 1,3-diisopropylbenzene or divinylbenzene as described in the patent EP1237941 B1. Among the organolithium compounds comprising several carbon-lithium bonds, the reaction adduct between 1,3-diisopropenylbenzene and s-butyllithium is preferred.

Suitable organolithium initiators comprising one or more nitrogen-lithium bonds are, for example, lithium amides resulting from the reaction of an organolithium compound with an acyclic or cyclic, preferably cyclic, secondary amine, dilithium amides resulting from the reaction of an organolithium compound with a compound comprising two nitrogen-containing groups, for example pyridinyl groups, such as 1,8-bis(6-ethyl-2-pyridyl)octane dilithium resulting from the reaction of 1,8-bis(6-ethyl-2-pyridyl)octane with tert-butyllithium.

Mention may be made, as secondary amine which can be used to prepare the initiators, of dimethylamine, diethylamine, dipropylamine, di(n-butyl)amine, di(sec-butyl)amine, dipentylamine, dihexylamine, di(n-octyl)amine, di(2-ethylhexyl)amine, dicyclohexylamine, N-methylbenzylamine, diallylamine, morpholine, piperazine, 2,6-dimethylmorpholine, 2,6-dimethylpiperazine, 1-ethylpiperazine, 2-methylpiperazine, 1-benzylpiperazine, piperidine, 3,3-dimethylpiperidine, 2,6-dimethylpiperidine, 1-methyl-4-(methylamino)piperidine, 2,2,6,6-tetramethylpiperidine, pyrrolidine, 2,5-dimethylpyrrolidine, azetidine, hexamethyleneimine, heptamethyleneimine, 5-benzyloxyindole, 3-azaspiro[5.5]undecane, 3-azabicyclo[3.2.2]nonane, carbazole, bistrimethylsilylamine, pyrrolidine and hexamethyleneamine. The secondary amine, when it is cyclic, is preferably chosen from pyrrolidine and hexamethyleneamine. The organolithium compound is preferably ethyllithium, n-butyllithium (n-BuLi), s-butyllithium (s-BuLi), isobutyl lithium, etc.

The [polar agent/alkali metal of the anionic initiator] molar ratio is greater than 0.1, advantageously greater than 0.3, more advantageously greater than 0.4. The [polar agent/alkali metal of the anionic initiator] molar ratio may range up to 3, advantageously up to 2.

When the polar agent is a tetraalkyldiamine, such as TMEDA, and the anionic initiator is an alkyllithium compound, the [polar agent/lithium of the anionic initiator] molar ratio is advantageously greater than 0.3, more advantageously greater than 0.4. The [polar agent/lithium of the anionic initiator] molar ratio may advantageously range up to 3, more advantageously up to 2.

I1.3 Polymerization Temperature

In the process according to the invention, the polymerization temperature is below 80° C. Indeed, it was observed that beyond this temperature, the degree of insertion of the cyclic diene monomer is low, the copolymer obtained comprising, relative to the total number in moles of units, less than 5 mol % of units derived from this cyclic diene monomer.

The polymerization temperature is advantageously below 75° C., more advantageously below 70° C.

The polymerization temperature advantageously varies from 45° C. to 70° C., more advantageously from 50° C. to 60° C.

I. 1.4 Other Process Parameters

The polymerization is preferably carried out in the presence of an inert hydrocarbon-based solvent which may, for example, be an aliphatic or alicyclic hydrocarbon, such as pentane, hexane, heptane, isooctane, cyclohexane or methylcyclohexane, or an aromatic hydrocarbon, such as benzene, toluene or xylene.

I.1.5 Post-Polymerization Step

The polymerization reaction makes it possible to prepare a living diene polymer. According to a variant of the invention, the polymerization reaction is then stopped by the deactivation of the living chains in a conventional manner. In order to stop the polymerization reaction, it is known to those skilled in the art to introduce a protic compound. By way of example, mention may be made of alcohols such as methanol, phenols such as hydroquinone or resorcinol, hydroxylamines such as N,N-diethylhydroxylamine.

According to another variant of the invention, the living polymer derived from the polymerization reaction may then be modified in order to prepare a functionalized, coupled or star-branched polymer depending on the nature of the modifying agent used. This post-polymerization modification is carried out in a manner known per se by addition of a functionalizing, coupling and/or star-branching agent to the living polymer chains or vice versa.

The functionalizing agents may for example introduce one or more nonpolar functions within the polymer. Such agents are known per se, such as, for example, $Me_2SiCl_2$, MeSiCl$_3$, SiCl$_4$, 1,6-bis(trichlorosilyl)hexane, Bu$_2$SnCl$_2$, SnCl$_4$, etc. This type of functionalization improves, for example in a tyre composition, the interaction between the filler and the elastomer or else certain properties of the functionalized elastomer. The functionalizing agents may also introduce one or more polar functions within the polymer. The polar function may be chosen, for example, from functions of the following type: amine, silanol, epoxide, ether, ester, hydroxyl, carboxylic acid, alkoxysilane or alkoxysilane substituted by another function, in particular amine or thiol, etc. These functions improve, in particular in a tyre composition, the interaction between an inorganic filler and the elastomer.

It is possible to obtain a mixture of polymer chains bearing different functions by successively reacting different functionalizing agents. For example, it is possible to initially react the living chains with an agent that introduces a nonpolar function based on silicon or tin, then to react the remaining living chains with a functionalizing agent that introduces a polar function.

The group resulting from the post-polymerization modification may be located at the chain end. It will then be said that the polymer is functionalized at the chain end. It is generally a polymer obtained by reaction of a living elastomer with an at least monofunctional molecule in order to react with a living chain end, the function being any type of chemical group known by a person skilled in the art, in particular as mentioned above.

The group resulting from the post-polymerization modification may be located in the main elastomer chain. It will then be said that the polymer is coupled. It is generally a polymer obtained by reaction of a living polymer with a coupling agent, i.e. any at least difunctional molecule in order to react with a living chain end, the function being any type of chemical group known by a person skilled in the art, in particular as mentioned above.

The group resulting from the post-polymerization modification may be central, to which n polymer chains or branches (n>2) are bonded, forming a star-branched structure of the polymer. It will then be said that the polymer is n-arm star-branched. It is generally a polymer obtained by reaction of a living polymer with a star-branching agent, i.e. any multifunctional molecule in order to react with a living chain end, the function being any type of chemical group known by a person skilled in the art, in particular as mentioned above.

I.1.6 Pre-Polymerization Step

Prior to the polymerization step, the process according to the invention may comprise a step of synthesizing methylenecyclopentene from myrcene by ring-closing metathesis.

Myrcene is a monoterpene available from plants. It can be extracted from essential oils of various plants such as pine, juniper or else mint. It is therefore a non-petrochemical renewable raw material favourable for sustainable development.

The process according to the invention can be carried out continuously or batchwise.

The copolymer obtained by the process according to the invention is advantageously an elastomer.

I.2 Copolymer According to the Invention

Another subject of the present invention is a random copolymer comprising, randomly distributed within the main linear chain of the copolymer, unsaturated units derived from at least one acyclic diene monomer and cyclic units derived from at least one cyclic diene monomer of which one C=C double bond is endocyclic and conjugated to an exocyclic C=C double bond.

In particular, this copolymer is capable of being obtained by the process according to the invention.

The random copolymer may also comprise units derived from another monomer. The copolymer according to the invention comprises units derived from the monomers described above. It is well known that the acyclic conjugated diene can be inserted as several 1,2 or 1,4 moieties or in the form of a ring. The cyclic conjugated diene can itself also be inserted as 1,2 or 1,4 moieties. In particular, the cyclic conjugated diene is inserted in the form of a ring comprising an endocyclic double bond or in the form of a ring comprising an exocyclic double bond.

The copolymer is advantageously an elastomer.

In the copolymer according to the invention, the molar percentage of units derived from the cyclic diene monomer, relative to the total number of units, is advantageously at least 5%, more advantageously at least 10%. In the copolymer according to the invention, the molar percentage of units derived from the cyclic diene monomer, relative to the total number of units, is advantageously less than 50%, more advantageously less than 30%.

In the copolymer according to the invention, the molar percentage of units derived from the acyclic diene monomer, relative to the total number of units, is advantageously at least 50%, more advantageously at least 70%. In the copolymer according to the invention, the molar percentage of units derived from the acyclic diene monomer, relative to the total number of units, is advantageously less than 95%, more advantageously less than 90%.

The copolymer according to the invention has a glass transition temperature Tg of between 0° C. and −70° C.

I.3 Compositions According to the Invention

Another subject of the present invention is a composition comprising the copolymer according to the invention. The composition is advantageously a rubber composition, especially a composition which can be used in the manufacture of a tyre. The composition may also comprise one or more of the following components:

a nanometric or reinforcing filler, a crosslinking system, a "diene" second elastomer or rubber, various additives usually present in tyre compositions.

Another subject of the present invention is a tyre, of which one of its constituent elements comprises a composition according to the invention.

II—Exemplary Embodiments of the Invention

The polymers are characterized, before curing, as indicated below.

Size Exclusion Chromatography:

Size exclusion chromatography (SEC) is used. SEC makes it possible to separate macromolecules in solution according to their size through columns filled with a porous gel. The macromolecules are separated according to their hydrodynamic volume, the bulkiest being eluted first.

Without being an absolute method, SEC makes it possible to comprehend the distribution of the molar masses of a polymer. The various number-average molar masses ($M_n$) and weight-average molar masses ($M_w$) can be determined from commercial standards and the polydispersity index ($PI=M_w/M_n$) can be calculated via a "Moore" calibration.

Preparation of the polymer: there is no specific treatment of the polymer sample before analysis. The latter is simply dissolved, in (tetrahydrofuran+1 vol % of diisopropylamine+1 vol % of triethylamine+1 vol % of distilled water) or in chloroform, at a concentration of approximately 1 g/l. The solution is then filtered through a filter with a porosity of 0.45 μm before injection.

SEC analysis: the apparatus used is a Waters Alliance chromatograph. The elution solvent is tetrahydrofuran+1 vol % of diisopropylamine+1 vol % of triethylamine or chloroform depending on the solvent used for dissolving the polymer. The flow rate is 0.7 ml/min, the temperature of the system is 35° C. and the analysis time is 90 min. A set of four Waters columns in series (a Styragel HMW7 column, a Styragel HMW6E column and two Styragel HT6E columns) is used.

The injected volume of the solution of the polymer sample is 100 μl. The detector is a Waters 2410 differential refractometer and the software for processing the chromatographic data is the Waters Empower system.

The calculated average molar masses are relative to a calibration curve produced from PSS Ready Cal-Kit commercial polystyrene standards.

Glass Transition Temperature:

The glass transition temperatures Tg of the polymers are measured using a differential scanning calorimeter. The analysis is carried out according to the requirements of the ASTM D3418-08 (2008) standard.

Determination of the Microstructure by $^1H$ and $^{13}C$ NMR Spectroscopy:

The contents of the various monomer units and their microstructures within the copolymer are determined by an NMR analysis. The spectra are acquired on a Bruker Avance 500 MHz spectrometer equipped with a "Broad Band" BBIz-grad 5 mm probe. Firstly, the characterization of the species is obtained from 1D, 1H and 2D $^1H$-$^{13}C$ HSQC and HMBC correlation experiments. Then, the microstructures are determined from $^1H$-decoupled $^{13}C$ spectra. The samples are dissolved in chloroform $CDCl_3$.

The spectral allocation of the $^1H$ and $^{13}C$ signals is listed in the table below:

| δ $^1H$ (ppm) | Number of 1H | Allocation |
|---|---|---|
| 4.5 to 4.8 | 2 | =CH2 of the methylenecyclopentene |
| 4.8 to 5.1 | 2 + 2 | 1,2PB + PB rings |
| 5.1 to 5.6 | 2 + 1 | 1,4PB + 1,2PB |
| 5.6 to 6.0 | 1 | PB rings |

| δ $^{13}C$ (ppm) | Number of 13C | Allocation |
|---|---|---|
| 104.0 to 108.7 | 1 | =CH2 of the methylenecyclopentene |
| 111.7 to 113.1 | 1 | CH2=CH PB rings |
| 113.1 to 117.8 | 1 | CH2=CH 1,2PB |
| 124.6 to 133.2 | 2 | CH 1,4PB |
| 139.3 to 146.1 | 1 + 1 | CH2=CH PB rings + CH2=CH 1,2PB |
| 153.1 to 158.8 | 1 | Quaternary C of the methylenecyclopentene |

Degree of Conversion of the Monomers:

The degree of conversion of the monomers is determined at 24 hours by weighing an extract dried at 140° C. under a reduced pressure of 200 mmHg. It is expressed as a percentage.

EXAMPLE 1

Random Copolymer of 1,3-butadiene and 3-methylenecyclopentene (70/30 Proportion by Mass)

Added to a 250 millilitre reactor, maintained under a nitrogen pressure of 2 bar, containing 61 millilitres of methylcyclohexane, are 0.48 millilitres (i.e. 0.5 equivalents relative to active lithium) of a 0.1 mol/l solution of tetramethylethylenediamine (TMEDA) in methylcyclohexane, and also 2 g of 3-methylenecyclopentene (MCP) and 4.7 g of butadiene (BTD). After neutralization of the impurities in the solution to be polymerized by addition of s-butyllithium, 1.12 millilitres of 0.085 mol/l s-butyllithium are added. The reaction medium then takes on a yellow color. The polymerization is carried out at 50° C. After 24 hours, the degree of conversion of the monomers reaches 86%.

The polymerization is stopped by adding an excess of methanol relative to lithium: a complete discoloration of the reaction medium is observed. The polymer solution is subjected to an antioxidant treatment by addition of 0.4 parts per hundred parts of elastomers (phr) of a 100 g/l solution in toluene of 4,4'-methylenebis(2,6-tert-butylphenol) and N-(1,3-dimethylbutyl)-N'-phenyl-p-phenylenediamine in 80/20 proportions by mass, then the polymer is dried by baking at 50° C. under vacuum/nitrogen for two days.

The relative molecular mass Mn of this copolymer is 31 700 g/mol and the PI is 1.07. The microstructure is as follows (PB=polybutadiene): 43.7 $_{mol}$% of 1,4-PB throughout the copolymer, 43.4 $_{mol}$% of 1,2-PB throughout the copolymer and 12.3 $_{mol}$% of MCP throughout the copolymer.

The glass transition temperature Tg of this copolymer is −47° C.

By following this protocol but by varying the polymerization temperature and/or the number of molar equivalents of TMEDA, relative to the lithium of the initiator, other copolymers are prepared. The characteristics of the synthesized copolymers are reported in the following table:

TABLE 1

| | | ¹³C NMR results | | | | Conversion/DSC | |
|---|---|---|---|---|---|---|---|
| Operating conditions | | mol % 1,4- | mol % 1,2- | mol % PB | mol % | | |
| T° (° C.) | Equivalents of TMEDA | PB/ (PB + MCP) | PB/ (PB + MCP) | ring/ (PB + MCP) | MCP/ (PB + MCP) | % Conv | Tg (° C.) |
| 50 | 0.5 | 43.7 | 43.4 | 0.6 | 12.3 | 86 | −47 |
|  | 1 | 29.2 | 54.9 | 2 | 13.9 | 91 | −29 |
|  | 2 | 21.1 | 62.2 | 1.9 | 14.8 | 90 | −20 |
| 60 | 2 | 26.7 | 57.3 | 1.6 | 14.4 | 87 | −24 |
| 70 | 1 | 39.5 | 46.6 | 1.5 | 12.4 | 85 | −42 |
| 90* | 0.4 | 66.3 | 28.2 | 1.5 | 4.0 | 74 | −72 |

*outside the invention

It is observed that when the polymerization temperature increases, the degree of insertion of 3-methylenecyclopentene decreases.

EXAMPLE 2

Random Copolymer of 1,3-butadiene and 3-methylenecyclopentene (50/50 Proportion by Mass and 2 eq/Li of Polar Agent)

Added to a 250 millilitre reactor, maintained under a nitrogen pressure of 2 bar, containing 61 millilitres of methylcyclohexane, are 1.14 millilitres (i.e. 2 equivalents relative to active lithium) of a 0.1 mol/l solution of tetramethylethylenediamine (TMEDA) in methylcyclohexane, and also 2 g of 3-methylenecyclopentene (MCP) and 2 g of butadiene (BTD). After neutralization of the impurities in the solution to be polymerized by addition of s-butyllithium, 0.67 millilitres of 0.085 mol/l s-butyllithium are added. The reaction medium then takes on a yellow color. The polymerization is carried out at 50° C. After 24 hours, the degree of conversion of the monomers reaches 96%.

The polymerization is stopped by adding an excess of methanol relative to lithium: a complete discoloration of the reaction medium is observed. The polymer solution is subjected to an antioxidant treatment by addition of 0.4 parts per hundred parts of elastomers (phr) of a 100 g/l solution in toluene of 4,4'-methylenebis(2,6-tert-butylphenol) and N-(1, 3-dimethylbutyl)-N'-phenyl-p-phenylenediamine in 80/20 proportions by mass, then the polymer is dried by baking at 50° C. under vacuum/nitrogen for two days.

The relative molecular mass Mn of this copolymer is 30 550 g/mol and the PI is 1.33. The microstructure is as follows: 15.4 $_{mol}$% of 1,4-PB throughout the copolymer, 50.4 $_{mol}$% of 1,2-PB throughout the copolymer, 1.86 $_{mol}$% of PB ring throughout the copolymer and 32.3 $_{mol}$% of MCP throughout the copolymer.

The glass transition temperature Tg of this copolymer is −13° C.

EXAMPLE 3

Random Copolymer of 1,3-butadiene and 3-methylenecyclopentene (50/50 Proportion by Mass and 0.4 eq/Li of Polar Agent)

Added to a 250 millilitre reactor, maintained under a nitrogen pressure of 2 bar, containing 61 millilitres of methylcyclohexane, are 0.23 millilitres (i.e. 0.4 equivalents relative to active lithium) of a 0.1 mol/l solution of tetramethylethylenediamine (TMEDA) in methylcyclohexane, and also 2 g of 3-methylenecyclopentene (MCP) and 2 g of butadiene (BTD). After neutralization of the impurities in the solution to be polymerized by addition of s-butyllithium, 0.67 millilitres of 0.085 mol/l s-butyllithium are added. The reaction medium then takes on a yellow color. The polymerization is carried out at 50° C. After 24 hours, the degree of conversion of the monomers reaches 84%.

The polymerization is stopped by adding an excess of methanol relative to lithium: a complete discoloration of the reaction medium is observed. The polymer solution is subjected to an antioxidant treatment by addition of 0.4 parts per hundred parts of elastomers (phr) of a 100 g/l solution in toluene of 4,4'-methylenebis(2,6-tert-butylphenol) and N-(1, 3-dimethylbutyl)-N'-phenyl-p-phenylenediamine in 80/20 proportions by mass, then the polymer is dried by baking at 50° C. under vacuum/nitrogen for two days.

The relative molecular mass Mn of this copolymer is 26 700 g/mol and the PI is 1.3. The microstructure is: 41.5 $_{mol}$% of 1,4-PB throughout the copolymer, 37.1 $_{mol}$% of 1,2-PB throughout the copolymer and 21.4 $_{mol}$% of MCP throughout the copolymer. The glass transition temperature Tg of this copolymer is −44° C.

Comparative Example 1

Copolymerization of 1,3-butadiene and 3-methylenecyclopentene (70/30 Proportion by Mass and Without Polar Agent)

Added to a 250 millilitre reactor, maintained under a nitrogen pressure of 2 bar, containing 61 millilitres of methylcyclohexane, are 2 g of 3-methylenecyclopentene (MCP) and 4.7 g of butadiene (BTD). After neutralization of the impurities in the solution to be polymerized by addition of s-butyllithium, 1.12 millilitres of 0.085 mol/l s-butyllithium are added. The reaction medium then takes on a yellow color. The polymerization is carried out at 50° C. After 24 hours, the degree of conversion of the monomers reaches 65%.

The polymerization is stopped by adding an excess of methanol relative to lithium: a complete discoloration of the reaction medium is observed. The polymer solution is subjected to an antioxidant treatment by addition of 0.4 parts per hundred parts of elastomers (phr) of a 100 g/l solution in toluene of 4,4'-methylenebis(2,6-tert-butylphenol) and N-(1, 3-dimethylbutyl)-N'-phenyl-p-phenylenediamine in 80/20 proportions by mass, then the polymer is dried by baking at 50° C. under vacuum/nitrogen for two days.

The relative molecular mass Mn of this copolymer is 29 500 g/mol and the PI is 1.15.

The microstructure, determined by $^{13}$C NMR spectroscopy, is as follows: 93.2 mol % of 1,4-PB throughout the copolymer, 6.8 $_{mol}$% of 1,2-PB throughout the copolymer and 0 $_{mol}$% of MCP throughout the copolymer.

The glass transition temperature Tg of this polymer is −73° C.

Comparative Example 2

Copolymerization of 1,3-butadiene and 1,3-cyclohexadiene (63/37 Proportion by Mass and 1.7 eq/Li of Polar Agent)

Added to a 250 millilitre reactor, maintained under a nitrogen pressure of 2 bar, containing 54 millilitres of toluene, are 3.18 millilitres (i.e. 1.7 equivalents relative to active lithium) of a 0.214 mol/l solution of 1,4-diazabicyclo[2.2.2]octane (DABCO) in methylcyclohexane, and also 2.2 g of 1,3-cyclohexadiene and 3.8 g of butadiene. After neutralization of the impurities in the solution to be polymerized by addition of s-butyllithium, 3.92 millilitres of 0.102 mol/l s-butyllithium are added. The reaction medium then takes on a yellow color. The polymerization is carried out at 25° C.

After 1.5 hours, the degree of conversion of the monomers reaches 62% (sample 1). After 24 hours, the degree of conversion of the monomers reaches 99% (sample 2). The polymerization is stopped by adding an excess of methanol relative to lithium: a complete discoloration of the reaction medium is observed. The polymer solution is subjected to an antioxidant treatment by addition of 0.4 parts per hundred parts of elastomers (phr) of a 100 g/l solution in toluene of 4,4'-methylenebis(2,6-tert-butylphenol) and N-(1,3-dimethylbutyl)-N'-phenyl-p-phenylenediamine in 80/20 proportions by mass, then the polymer is dried by baking at 50° C. under vacuum/nitrogen for two days.

| | Degree of monomer conversion (%) | Content of 1,4-butadiene (mol %)[1] | Content of 1,2-butadiene (mol %)[1] | Content of cyclohexadiene (mol %)[1] | Molecular mass Mn (g/mol) (PI)[2] |
|---|---|---|---|---|---|
| Sample 1 | 62 | 55 | 45 | 0 | 9500 (1.03) |
| Sample 2 | 99 | 41 | 34 | 25 | 13000 (1.08) |

[1] Determined by $^1$H NMR spectroscopy.
[2] Determined by SEC chromatography.

The insertion of cyclohexadiene takes place predominantly at the end of polymerization. It is not therefore random. A block copolymer is obtained.

The invention claimed is:

1. A process for preparing a random copolymer based on at least one acyclic diene monomer and on at least one cyclic diene monomer, wherein the process comprises a step of copolymerization, in the presence of a polar agent and an anionic initiator in a polymerization solvent, of at least one acyclic diene monomer and of at least one cyclic diene monomer of which one C═C double bond is endocyclic and conjugated to an exocyclic C═C double bond, at a polymerization temperature below 80° C., and a molar ratio of the polar agent/function(s) of the anionic initiator capable of initiating anionic polymerization being greater than 0.1.

2. A process according to claim 1, wherein the at least one cyclic diene monomer includes a monomer corresponding to the following formula (I):

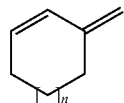

where n=0 or 1.

3. A process according to claim 1, wherein the molar ratio is greater than or equal to 0.3.

4. A process according to claim 1, wherein the at least one acyclic diene monomer includes a conjugated diene monomer.

5. A process according to claim 1, wherein a vinylaromatic compound having from 8 to 20 carbon atoms is also copolymerized.

6. A process according to claim 1, wherein the polar agent is a tetraalkyldiamine.

7. A process according to claim 1, wherein the anionic initiator contains an alkali metal.

8. A process according to claim 1, wherein the polymerization temperature varies from 45° C. to 70° C.

9. A copolymer capable of being obtained by the process defined according to claim 2.

10. A random copolymer comprising, randomly distributed within a main linear chain of the copolymer, unsaturated units derived from at least one acyclic diene monomer and cyclic units derived from at least one cyclic diene monomer of which one C═C double bond is endocyclic and conjugated to an exocyclic C═C double bond, wherein the cyclic diene monomer is a monomer corresponding to the following formula (I):

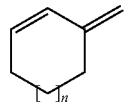

where n=0 or 1.

11. A copolymer according to claim 10, wherein the copolymer also comprises units derived from a vinylaromatic compound having from 8 to 20 carbon atoms.

12. A copolymer according to claim 10, wherein the molar percentage of units derived from the cyclic diene monomer, relative to the total number of units, is at least 5%.

13. A copolymer according to claim 10, wherein the molar percentage of units derived from the cyclic diene monomer, relative to the total number of units, is less than 50%.

14. A copolymer according to claim 10, wherein said copolymer is an elastomer.

15. A copolymer according to claim 10, wherein the cyclic diene monomer is 3-methylenecyclopentene.

16. A copolymer according to claim 10, wherein the acyclic diene monomer is a conjugated diene monomer.

17. A copolymer according to claim 16, wherein the acyclic diene monomer is 1,3-butadiene or isoprene.

18. A composition comprising the copolymer defined according to claim 10.

19. A tire, of which one of its constituent elements comprises a composition according to claim 18.

* * * * *